United States Patent [19]

Cherpeck

[11] Patent Number: 5,466,268
[45] Date of Patent: Nov. 14, 1995

[54] POLYALKYL AND POLYALKENYL AROMATIC AMIDES AND FUEL COMPOSITIONS CONTAINING THE SAME

[75] Inventor: Richard E. Cherpeck, Cotati, Calif.

[73] Assignee: Chevron Chemical Company, San Ramon, Calif.

[21] Appl. No.: 366,528

[22] Filed: Dec. 30, 1994

[51] Int. Cl.[6] .............................. C10L 1/22; C07C 237/28
[52] U.S. Cl. ........................ 44/419; 44/323; 564/153; 564/155; 564/157; 564/163; 564/166; 564/167
[58] Field of Search .................. 44/419, 323; 564/155, 564/157, 163

[56] References Cited

U.S. PATENT DOCUMENTS

| | | | |
|---|---|---|---|
| 2,714,607 | 8/1955 | Matter | 260/471 |
| 3,285,855 | 11/1966 | Dexter et al. | 252/57 |
| 3,338,833 | 8/1967 | Spivak et al. | 44/419 |
| 3,434,814 | 3/1969 | Dubeck et al. | 44/69 |
| 3,849,085 | 11/1974 | Kreuz et al. | 44/78 |
| 3,894,849 | 7/1975 | Polss | 44/419 |
| 4,134,846 | 1/1979 | Machleder et al. | 252/51.5 A |
| 4,177,041 | 12/1979 | Sung et al. | 44/419 |
| 4,231,759 | 11/1980 | Udelhofen et al. | 44/75 |
| 4,303,673 | 12/1981 | Biedermann et al. | 564/155 |
| 4,320,021 | 3/1982 | Lange | 252/51.5 R |
| 4,328,322 | 5/1982 | Baron | 521/163 |
| 4,347,148 | 8/1982 | Davis | 252/51.5 R |
| 4,639,255 | 1/1987 | Schuettenberg et al. | 44/419 |
| 4,737,159 | 4/1988 | Phillips | 44/419 |
| 4,859,210 | 8/1989 | Franz et al. | 44/53 |
| 5,090,914 | 2/1992 | Reardan et al. | 435/188 |
| 5,196,142 | 3/1993 | Mollet et al. | 252/311 |
| 5,310,760 | 5/1994 | Washburn et al. | 564/163 |

*Primary Examiner*—Ellen McAvoy
*Attorney, Agent, or Firm*—C. J. Caroli

[57] ABSTRACT

Polyalkyl and polyalkenyl aromatic amides having the formula:

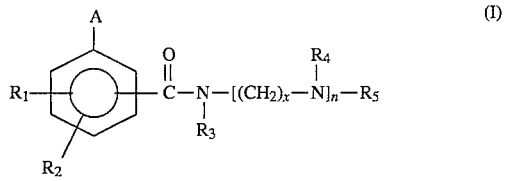

or a fuel-soluble salt thereof; wherein A is hydroxy, nitro, amino, N-alkylamino wherein the alkyl group contains 1 to 6 carbon atoms, or N,N-dialkylamino wherein each alkyl group independently contains 1 to 6 carbon atoms; $R_1$ and $R_2$ are each independently hydrogen, hydroxy, lower alkyl having 1 to 6 carbon atoms, or lower alkoxy having 1 to 6 carbon atoms; $R_3$ is hydrogen or lower alkyl having 1 to 6 carbon atoms; $R_4$ is hydrogen or an acyl group of the formula:

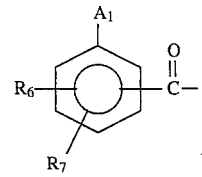

wherein $A_1$ is hydroxy, nitro, amino, N-alkylamino wherein the alkyl group contains 1 to 6 carbon atoms, or N,N-dialkylamino wherein each alkyl group independently contains 1 to 6 carbon atoms; $R_6$ and $R_7$ are each independently hydrogen, hydroxy, lower alkyl having 1 to 6 carbon atoms, or lower alkoxy having 1 to 6 carbon atoms; $R_5$ is a polyalkyl or polyalkenyl group having an average molecular weight in the range of about 450 to 5,000; n is an integer from 0 to 2; and x is an integer from 2 to 5.

The polyalkyl and polyalkenyl aromatic amides of formula I are useful as fuel additives for the prevention and control of engine deposits.

52 Claims, No Drawings

POLYALKYL AND POLYALKENYL AROMATIC AMIDES AND FUEL COMPOSITIONS CONTAINING THE SAME

BACKGROUND OF THE INVENTION

1. Field of the Invention

This invention relates to novel hydroxy, nitro, and amino aromatic compounds. More particularly, this invention relates to novel polyalkyl and polyalkenyl hydroxy, nitro, and amino aromatic amides and their use in fuel compositions to prevent and control engine deposits.

2. Description of the Related Art

It is well known that automobile engines tend to form deposits on the surface of engine components, such as carburetor ports, throttle bodies, fuel injectors, intake ports, and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to 0.25 volume percent of a high molecular weight aliphatic hydrocarbon-substituted phenol in which the aliphatic hydrocarbon radical has an average molecular weight in the range of about 500 to 3,500. This patent teaches that gasoline compositions containing minor amounts of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

Similarly, U.S. Pat. No. 4,134,846, issued Jan. 16, 1979 to Machleder et al., discloses a fuel additive composition comprising a mixture of (1) the reaction product of an aliphatic hydrocarbon-substituted phenol, epichlorohydrin and a primary or secondary mono- or polyamine, and (2) a polyalkylene phenol. This patent teaches that such compositions show excellent carburetor, induction system and combustion chamber detergency and, in addition, provide effective rust inhibition when used in hydrocarbon fuels at low concentrations.

Amino phenols are also known to function as detergents/dispersants, antioxidants, and anti-corrosion agents when used in fuel compositions. U.S. Pat. No. 4,320,021, issued Mar. 16, 1982 to R. M. Lange, for example, discloses amino phenols having at least one substantially saturated hydrocarbon-based substituent of at least 30 carbon atoms. The amino phenols of this patent are taught to impart useful and desirable properties to oil-based lubricants and normally liquid fuels.

Nitro phenols have also been employed as fuel additives. For example, U.S. Pat. No. 4,347,148, issued Aug. 31, 1982 to K. E. Davis, discloses nitro phenols containing at least one aliphatic substituent having at least about 40 carbon atoms. The nitro phenols of this patent are taught to be useful as detergents, dispersants, antioxidants, and demulsifiers for lubricating oil and fuel compositions.

Similarly, U.S. Pat. No. 3,434,814, issued Mar. 25, 1969 to M. Dubeck et al., discloses a liquid hydrocarbon fuel composition containing a major quantity of a liquid hydrocarbon of the gasoline boiling range and a minor amount sufficient to reduce exhaust emissions and engine deposits of an aromatic nitro compound having an alkyl, aryl, aralkyl, alkanoyloxy, alkoxy, hydroxy, or halogen substituent.

Poly(oxyalkylene) esters of amino- and nitrobenzoic acids are also known in the art. For example, U.S. Pat. No. 2,714,607, issued Aug. 2, 1955 to M. Matter, discloses polyethoxy esters of aminobenzoic acids, nitrobenzoic acids, and other isocyclic acids. These polyethoxy esters are taught to have excellent pharmacological properties and to be useful as anesthetics, spasmolytics, analeptics, and bacteriostatics.

Similarly, U.S. Pat. No. 5,090,914, issued Feb. 25, 1992 to D. T. Reardan et al., discloses poly(oxyalkylene) aromatic compounds having an amino or hydrazinocarbonyl substituent on the aromatic moiety and an ester, amide, carbamate, urea, or ether linking group between the aromatic moiety and the poly(oxyalkylene) moiety. These compounds are taught to be useful for modifying macromolecular species such as proteins and enzymes.

U.S. Pat. No. 4,328,322, issued Sep. 22, 1980 to R. C. Baron, discloses amino- and nitrobenzoate esters of oligomeric polyols, such as poly(ethylene) glycol. These materials are used in the production of synthetic polymers by reaction with a polyisocyanate.

In addition, U.S. Pat. No. 4,231,,759 issued Nov. 4, 1980 to Udelhofen et al., discloses a fuel additive composition comprising the Mannich condensation product of (1) a high molecular weight alkyl-substituted hydroxyaromatic compound wherein the alkyl group has a number average molecular weight of about 600 to about 3,000, (2) an amine, and (3) an aldehyde. This patent teaches that such Mannich condensation products provide carburetor cleanliness when employed alone, and intake valve cleanliness when employed in combination with a hydrocarbon carrier fluid.

U.S. Pat. No. 4,859,210, issued Aug. 22, 1989 to Franz et al., discloses fuel compositions containing (1) one or more polybutyl or polyisobutyl alcohols wherein the polybutyl or polyisobutyl group has a number average molecular weight of 324 to 3,000, or (2) a poly(alkoxylate) of the polybutyl or polyisobutyl alcohol, or (3) a carboxylate ester of the polybutyl or polyisobutyl alcohol. This patent further teaches that when the fuel composition contains an ester of a polybutyl or polyisobutyl alcohol, the ester-forming acid group may be derived from saturated or unsaturated, aliphatic or aromatic, acyclic or cyclic, mono- or polycarboxylic acids.

U.S. Pat. No. 3,285,855, issued Nov. 15, 1966 to Dexter et al., discloses alkyl esters of dialkyl hydroxybenzoic and hydroxyphenylalkanoic acids wherein the ester moiety contains from 6 to 30 carbon atoms. This patent teaches that such esters are useful for stabilizing polypropylene and other organic material normally subject to oxidative deterioration. Similar alkyl esters containing hindered dialkyl hydroxyphenyl groups are disclosed in U.S. Pat. No. 5,196,565, which issued Mar. 23, 1993 to Ross.

U.S. Pat. No. 5,196,142, issued Mar. 23, 1993 to Mollet et al., discloses alkyl esters of hydroxyphenyl carboxylic acids wherein the ester moiety may contain up to 23 carbon atoms. This patent teaches that such compounds are useful as antioxidants for stabilizing emulsion-polymerized polymers.

It has now been discovered that certain polyalkyl and polyalkenyl hydroxy, nitro, and amino aromatic amides provide excellent control of engine deposits, especially intake valve deposits, when employed as fuel additives in fuel compositions.

SUMMARY OF THE INVENTION

The present invention provides novel polyalkyl and polyalkenyl hydroxy, nitro, and amino aromatic amides which are useful as fuel additives for the prevention and control of engine deposits, particularly intake valve deposits.

The polyalkyl and polyalkenyl hydroxy, nitro, and amino aromatic amides of the present invention have the formula:

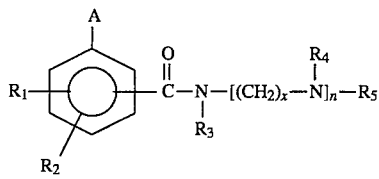

or a fuel-soluble salt thereof; wherein A is hydroxy, nitro, amino, N-alkylamino wherein the alkyl group contains 1 to 6 carbon atoms, or N,N-dialkylamino wherein each alkyl group independently contains 1 to 6 carbon atoms; $R_1$ and $R_2$ are each independently hydrogen, hydroxy, lower alkyl having 1 to 6 carbon atoms, or lower alkoxy having 1 to 6 carbon atoms; $R_3$ is hydrogen or lower alkyl having 1 to 6 carbon atoms; $R_4$ is hydrogen or an acyl group of the formula:

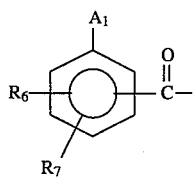

wherein $A_1$ is hydroxy, nitro, amino, N-alkylamino wherein the alkyl group contains 1 to 6 carbon atoms, or N,N-dialkylamino wherein each alkyl group independently contains 1 to 6 carbon atoms; $R_6$ and $R_7$ are each independently hydrogen, hydroxy, lower alkyl having 1 to 6 carbon atoms, or lower alkoxy having 1 to 6 carbon atoms; $R_5$ is a polyalkyl or polyalkenyl group having an average molecular weight in the range of about 450 to 5,000; n is an integer from 0 to 2; and x is an integer from 2 to 5.

The present invention further provides a fuel composition comprising a major amount of hydrocarbons boiling in the gasoline or diesel range and an effective deposit-controlling amount of a polyalkyl or polyalkenyl hydroxy, nitro, or amino aromatic amide of the present invention.

The present invention additionally provides a fuel concentrate comprising an inert stable oleophilic organic solvent boiling in the range of from about 150° F. to 400° F. (about 65° C. to 205° C.) and from about 10 to 70 weight percent of a polyalkyl or polyalkenyl hydroxy, nitro, or amino aromatic amide of the present invention.

Among other factors, the present invention is based on the surprising discovery that certain polyalkyl and polyalkenyl hydroxy, nitro, and amino aromatic amides, when employed as fuel additives in fuel compositions, provide excellent control of engine deposits, especially on intake valves, and produce.

DETAILED DESCRIPTION OF THE INVENTION

The fuel additives provided by the present invention have the general formula:

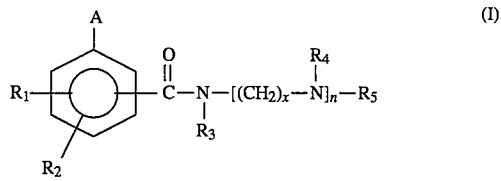

wherein A, $R_1$, $R_3$, $R_3$, $R_4$, $R_5$, n, and x are as defined hereinabove.

In formula I, above, A is preferably a hydroxy, nitro, or amino group. More preferably, A is a hydroxy group.

Preferably, $R_1$ is hydrogen, hydroxy, or lower alkyl having 1 to 4 carbon atoms. More preferably, $R_1$ is hydrogen or hydroxy. Most preferably, $R_1$ is hydrogen.

$R_2$ and $R_3$ are preferably hydrogen.

$R_4$ is hydrogen or an acyl group of the formula:

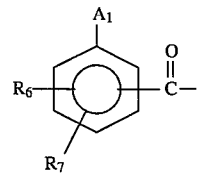

wherein $A_1$ is preferably a hydroxy, nitro, or amino group. More preferably, $A_1$ is a hydroxy group. Preferably, $R_6$ is hydrogen, hydroxy, or lower alkyl having 1 to 4 carbon atoms. More preferably, $R_6$ is hydrogen. $R_7$ is preferably hydrogen.

Preferably, $R_5$ is a polyalkyl or polyalkenyl group having an average molecular weight in the range of about 450 to 5,000, more preferably about 500 to 3,000, and most preferably about 600 to 2,000.

Preferably, n is 0 or 1.

Preferably, x is an integer from 2 to 3. More preferably, x is 2.

A preferred group of polyalkyl and polyalkenyl aromatic amides are those of formula I wherein $R_1$ and $R_6$ are hydrogen, hydroxy, or lower alkyl having 1 to 4 carbon atoms; $R_2$, $R_3$, and $R_7$ are hydrogen; n is 1 or 2; and x is 2.

Another preferred group of polyalkyl and polyalkenyl aromatic amides are those of formula I wherein $R_1$ and $R_6$ are hydrogen, hydroxy, or lower alkyl having 1 to 4 carbon atoms; $R_2$, $R_3$, and $R_7$ are hydrogen; and n is 0.

When A and $A_1$ are an N-alkylamino group, the alkyl group of the N-alkylamino moiety preferably contains 1 to 4 carbon atoms. More preferably, the alkyl group is methyl or ethyl. For example, particularly preferred N-alkylamino groups are N-methylamino and N-ethylamino groups. Most preferably, the alkyl group is methyl.

Similarly, when A and $A_1$ are an N,N-dialkylamino group, each alkyl group of the N,N-dialkylamino moiety preferably contains 1 to 4 carbon atoms. More preferably, each alkyl group is either methyl or ethyl. For example, particularly preferred N,N-dialkylamino groups are N,N-dimethylamino, N-ethyl-N-methylamino, and N,N-diethylamino groups. Most preferably, each alkyl group is methyl.

A further preferred group of polyalkyl and polyalkenyl aromatic amides are those wherein A and $A_1$ are hydroxy, $R_1$ and $R_6$ are hydrogen or hydroxy, $R_2$, $R_3$, and $R_7$ are hydrogen, n is 1 and x is 2. Another preferred group of polyalkyl and polyalkenyl aromatic amides are those wherein A is hydroxy, $R_1$ is hydrogen or hydroxy, $R_2$ and $R_3$ are hydrogen, and n is 0.

It is especially preferred that the hydroxy, nitro, amino, N-alkylamino, or N,N-dialkylamino substituent present in the aromatic moiety of the polyalkyl and polyalkenyl aromatic amides of this invention be situated in a meta or para position relative to the polyalkyl or polyalkenyl amide moiety. When $R_1$ and $R_6$ is a hydroxy or lower alkyl having 1 to 4 carbon atoms, it is particularly preferred that the hydroxy or lower alkyl groups be in a meta or para position relative to the polyalkyl or polyalkenyl amide moiety and in an ortho position relative to the hydroxy, nitro, amino, N-alkylamino, or N,N-dialkylamino substituent.

The polyalkyl and polyalkenyl aromatic amides of the present invention will generally have a sufficient molecular weight so as to be non-volatile at normal engine intake valve operating temperatures (about 200° C. to 250° C.). Typically, the molecular weight of the polyalkyl and polyalkenyl aromatic amides of this invention will range from about 450 to about 5,000, preferably from 500 to 3,000, more preferably from 600 to 2,000.

Fuel-soluble salts of the polyalkyl and polyalkenyl hydroxy aromatic amides of the present invention are also contemplated to be useful for preventing or controlling deposits. Such salts include alkali metal, alkaline earth metal, ammonium, substituted ammonium, and sulfonium salts. Preferred metal salts are the alkali metal salts, particularly the sodium and potassium salts, and the substituted ammonium salts, particularly tetraalkyl-substituted ammonium salts, such as the tetrabutylammonium salts.

Fuel-soluble salts of the polyalkyl and polyalkenyl amino aromatic amides of the present invention can be readily prepared for those compounds containing an amino, N-alkylamino, or N,N-dialkylamino group and such salts are contemplated to be useful for preventing or controlling engine deposits. Suitable salts include, for example, those obtained by protonating the amino moiety with a strong organic acid, such as an alkyl- or arylsulfonic acid. Preferred salts are derived from toluenesulfonic acid and methanesulfonic acid.

Definitions

As used herein, the following terms have the following meanings unless expressly stated to the contrary.

The term "amino" refers to the group: —$NH_2$.

The term "N-alkylamino" refers to the group: —$NHR_a$ wherein $R_a$ is an alkyl group. The term "N,N-dialkylamino" refers to the group: —$NR_bR_c$, wherein $R_b$ and $R_c$ are alkyl groups.

The term "alkyl" refers to both straight- and branched-chain alkyl groups.

The term "lower alkyl" refers to alkyl groups having 1 to about 6 carbon atoms and includes primary, secondary, and tertiary alkyl groups. Typical lower alkyl groups include, for example, methyl, ethyl, n-propyl, isopropyl, n-butyl, sec-butyl, t-butyl, n-pentyl, n-hexyl, and the like.

The terms "polyalkyl" and "polyalkenyl" refer to alkyl and alkenyl groups which are generally derived from polyolefins which are polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to carbon atoms. More preferred mono-olefins include propylene, butylene, particularly isobutylene, 1-octene, and 1-decene. Polyolefins prepared from such mono-olefins include polypropylene, polybutene, especially polyisobutene, and the polyalphaolefins produced from 1-octene and 1-decene.

General Synthetic Procedures

The polyalkyl and polyalkenyl hydroxy, nitro, and amino aromatic amides of this invention may be prepared by the following general methods and procedures. It should be appreciated that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

Moreover, those skilled in the art will recognize that it may be necessary to block or protect certain functional groups while conducting the following synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, *Protective Groups in Organic Synthesis*, Second Edition, Wiley, New York, 1991, and references cited therein.

In the present synthetic procedures, a hydroxy group will preferably be protected, when necessary, as the benzyl or tert-butyldimethylsilyl ether. Introduction and removal of these protecting groups is well described in the art. Amino groups may also require protection and this may be accomplished by employing a standard amino protecting group, such as a benzyloxycarbonyl or a trifluoroacetyl group. Additionally, as will be discussed in further detail hereinbelow, the polyalkyl and polyalkenyl aromatic amides of this invention having an amino group on the aromatic moiety will generally be prepared from the corresponding nitro derivative. Accordingly, in many of the following procedures, a nitro group will serve as a protecting group for the amino moiety.

The polyalkyl and polyalkenyl aromatic amides of the present invention having the formula:

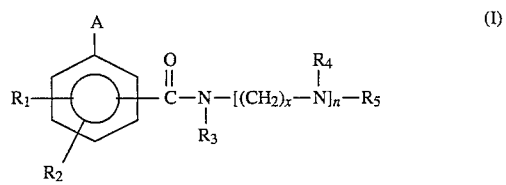 (I)

wherein A, $R_1$, $R_2$, $R_3$, $R_4$, $R_5$, n, and x are as defined above, may be prepared by conventional reaction conditions by reacting an acyl halide having the formula:

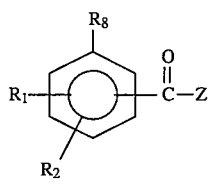

(II)

wherein $R_1$, and $R_2$ are as defined above, $R_8$ is a nitro or protected hydroxy or amino group, and Z is a halide, such as chloride or bromide, with a polyalkyl or polyalkenyl substituted amine having the formula:

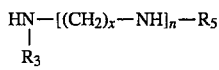

(III)

wherein $R_3$, $R_5$, n, and x are as defined above.

A. Preparation of the Acyl Halide

Acyl halides of formula II may be prepared from the corresponding aromatic carboxylic acids by first protecting the hydroxy or amino groups as necessary to form a carboxylic acid having the formula:

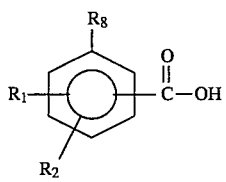

(IV)

wherein $R_1$ and $R_2$ are as defined above and $R_8$ is nitro or a suitably protected hydroxy or amino group.

The aromatic carboxylic acids which are first protected and then converted to the corresponding acyl halide are either known compounds or can be prepared from known compounds by conventional procedures. Representative aromatic carboxylic acids suitable for use as starting materials include, for example, 2-hydroxybenzoic acid, 3-hydroxybenzoic acid, 4-hydroxybenzoic acid, 3,4-dihydroxybenzoic acid, 3,4,5-trihydroxybenzoic acid, 3-hydroxy-4-methoxybenzoic acid, 4-hydroxy-3-methoxybenzoic acid, 3-t-butyl-4-hydroxybenzoic acid, 3,5-di-t-butyl- 4-hydroxybenzoic acid, 2-nitrobenzoic acid, 3-nitrobenzoic acid, 4-nitrobenzoic acid, 3-hydroxy-4-nitrobenzoic acid, 4-hydroxy-3-nitrobenzoic acid, 2-aminobenzoic acid (anthranilic acid), 3-aminobenzoic acid, 4-aminobenzoic acid, 3-amino-4-hydroxybenzoic acid, 4-amino-3-hydroxybenzoic acid, 3-amino-4-methoxybenzoic acid, 4-amino-3-methoxybenzoic acid, 4-amino-3-methylbenzoic acid, 4-amino-3,5-di-t-butylbenzoic acid, 3-(N-methylamino) benzoic acid, 4-(N-methylamino)benzoic acid, 3-(N-ethylamino) benzoic acid, 4-(N-ethylamino)benzoic acid, 3-(N,N-dimethylamino) benzoic acid, 4-(N,N-dimethylamino) benzoic acid, and the like.

Preferred aromatic carboxylic acids include 3-hydroxybenzoic acid, 4-amino-3-hydroxybenzoic acid, 3-nitrobenzoic acid, 4-nitrobenzoic acid, 3-hydroxy-4-nitrobenzoic acid, 4-hydroxy-3-nitrobenzoic acid, 3-aminobenzoic acid, 4-aminobenzoic acid, 3-amino-4-hydroxybenzoic acid, and 4-amino-3-hydroxybenzoic acid.

When the aromatic carboxylic acid contains a hydroxy group, for example, when A or $R_1$ is hydroxy, protection of the aromatic hydroxy groups may be accomplished using well-known procedures. The choice of a suitable protecting group for a particular hydroxy aromatic carboxylic acid will be apparent to those skilled in the art. Various protecting groups, and their introduction and removal, are described, for example, in T. W. Greene and P. G. M. Wuts, *Protective Groups in Organic Synthesis,* Second Edition, Wiley, New York, 1991, and references cited therein.

Deprotection of the aromatic hydroxy group(s) can also be accomplished using conventional procedures. Appropriate conditions for this deprotection step will depend upon the protecting group(s) utilized in the synthesis and will be readily apparent to those skilled in the art. For example, benzyl protecting groups may be removed by hydrogenolysis under 1 to about 4 atmospheres of hydrogen in the presence of a catalyst, such as palladium on carbon. Typically, this deprotection reaction is conducted in an inert solvent, preferably a mixture of ethyl acetate and acetic acid, at a temperature of from about 0° C. to about 40° C. for about 1 to about 24 hours.

When synthesizing the polyalkyl and polyalkenyl aromatic amides of formula I having an amino group on the aromatic moiety (i.e., where A is an amino group), it is generally desirable to first prepare the corresponding nitro compound (i.e., where A is a nitro group) and then to reduce the nitro group to an amino group using conventional procedures. Aromatic nitro groups may be reduced to amino groups using a number of procedures that are well known in the art. For example, aromatic nitro groups may be reduced under catalytic hydrogenation conditions; or by using a reducing metal, such as zinc, tin, iron, and the like, in the presence of an acid, such as dilute hydrochloric acid.

Generally, reduction of the nitro group by catalytic hydrogenation is preferred. Typically, this reaction is conducted using about 1 to 4 atmospheres of hydrogen and a platinum or palladium catalyst, such as palladium on carbon. The reaction is typically carried out at a temperature of about 0° C. to about 100° C. for about 1 to 24 hours in an inert solvent, such as ethanol, ethyl acetate, toluene, and the like. Hydrogenation of aromatic nitro groups is discussed in further detail in, for example, P. N. Rylander, *Catalytic Hydrogenation in Organic Synthesis,* pp. 113–137, Academic Press (1979); and *Organic Synthesis, Collective Vol. I,* Second Edition, pp. 240–241, John Wiley and Sons, Inc. (1941); and references cited therein.

In certain cases where the hydroxy aromatic carboxylic acids have bulky alkyl groups adjacent to the hydroxy group, such as 3,5-di-t-butyl-4-hydroxybenzoic acid, it will generally not be necessary to protect the hydroxy group prior to formation of the acyl halide, since such hydroxy groups are sufficiently sterically hindered so as to be substantially non-reactive with the halide moiety.

The acyl halide of formula II may then be prepared by reacting the protected aromatic carboxylic acid with an inorganic halide, such as thionyl chloride, phosphorous trichloride, phosphorous tribromide, or phosphorous pentachloride; or with oxalyl chloride, using conventional procedures.

Typically, this reaction will be conducted using about 1 to 5 molar equivalents of the inorganic acyl halide or oxalyl chloride, either neat or in an inert solvent, such as diethyl ether, at a temperature in the range of about 20° C. to about 80° C. for about 1 to about 48 hours. A catalyst, such as N,N-dimethylformamide, may also be used in this reaction.

B. Preparation of the Polyalkyl or Polyalkenyl Substituted Amine

The polyalkyl or polyalkenyl substituted amine of formula III comprises the reaction product of a polyalkyl or polyalkenyl halide derived from a polyolefin having an average molecular weight of about 450 to 5,000 and a nitrogen-containing compound selected from ammonia, a primary monoamine having from 1 to 6 carbon atoms, and a polyamine having from 2 to 3 nitrogen atoms and from 2 to carbon atoms.

As indicated above, the polyalkyl or polyalkenyl substituent on the polyalkenyl or polyalkenyl amine will have an average molecular weight in the range of about 450 to 5,000, preferably about 500 to 5,000, more preferably about 500 to 3,000, and most preferably about 600 to 2,000.

The polyalkyl or polyalkenyl substituent on the polyalkyl or polyalkenyl amine employed in the invention may be generally derived from polyolefins which are polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to 12 carbon atoms. More preferred mono-olefins include propylene, butylene, particularly isobutylene, 1-octene, and 1-decene. Polyolefins prepared from such mono-olefins include polypropylene, polybutene, especially polyisobutene, and the polyalphaolefins produced from 1-octene and 1-decene. Most preferred are polyolefins prepared from polyisobutene.

One type of suitable polyolefins are those containing an alkylvinylidene isomer present in an amount at least about 20%, and preferably at least 50% of the total polyolefin composition. The preferred alkylvinylidene isomers include methylvinylidene and ethylvinylidene, more preferably the methylvinylidene isomer.

Accordingly, high molecular weight polyolefins which may be used in this invention include polyisobutenes which comprise at least about 20% of the more reactive methylvinylidene isomer, preferably at least 50%, and more preferably at least 70%. Suitable polyisobutenes include those prepared using $BF_3$ catalysts. The preparation of such polyisobutenes in which the methylvinylidene isomer comprises a high percentage of the total composition is described in U.S. Pat. Nos. 4,152,499 and 4,605,808.

Examples of suitable polyisobutenes having a high alkylvinylidene content include Ultravis 30, a polyisobutene having a molecular weight of about 1300 and a methylvinylidene content of about 76%, available from British Petroleum.

The amine component of the polyalkyl or polyalkenyl substituted amine may be derived from ammonia, a primary monoamine, or a polyamine having terminal amino nitrogen atoms. Primary monoamines useful in preparing compounds of the present invention contain 1 nitrogen atom and from 1 to 6 carbon atoms. Examples of suitable monoamines include N-methylamine, N-ethylamine, N-n-propylamine, N-isopropylamine, N-n-butylamine, N-isobutylamine, N-sec-butylamine, N-tert-butylamine, N-n-pentylamine, and N-n-hexylamine. Preferred primary amines are N-methylamine, N-ethylamine, and N-n-propylamine.

When the amine component is derived from a polyamine, the polyamine will be either an alkylene diamine or a dialkylene triamine. The alkylene group will contain from 2 to 5 carbon atoms, preferably from 2 to 3 carbon atoms. Examples of such polyamines include ethylene diamine, propylene diamine, isopropylene diamine, butylene diamine, isobutylene diamine, pentylene diamine, diethylene triamine, dipropylene triamine, diisopropylene triamine, dibutylene triamine, diisobutylene triamine, and dipentylene triamine. Preferred polyamines are ethylene diamine and diethylene triamine.

Particularly preferred polyalkyl and polyalkenyl substituted amines include polyisobutenyl ethylene diamine and polyisobutyl amine, wherein the polyisobutyl group is substantially saturated and the amine moiety is derived from ammonia.

The polyalkyl and polyalkenyl substituted amines employed to make the aromatic amides of this invention are prepared by conventional procedures known in the art. Such polyalkyl substituted amines and their preparations are described in detail in U.S. Pat. Nos. 3,438,757; 3,565,804; 3,574,576; 3,898,056; 3,960,515; and 4,832,702, the disclosures of which are incorporated herein by reference for all purposes.

C. Preparation of the Polyalkyl or Polyalkenyl Aromatic Amide

Reaction of the acyl halide of formula II with a polyalkyl or polyalkenyl substituted amine of formula III provides a polyalkyl or polyalkenyl aromatic amide of formula I.

Typically, this reaction is conducted by contacting a polyalkyl or polyalkenyl substituted amine with about 1.0 to about 3.5 molar equivalents of an acyl halide of formula II in an inert solvent, such as toluene, dichloromethane, diethyl ether, and the like, at a temperature in the range of about 25° C. to about 150° C. The reaction is generally complete in about 0.5 to about 48 hours. Preferably, the reaction is conducted in the presence of a sufficient amount of an amine capable of neutralizing the acid generated during the reaction, such as triethylamine, di(isopropyl)ethylamine, pyridine, or 4-dimethylamino-pyridine.

Fuel Compositions

The polyalkyl and polyalkenyl aromatic amides of the present invention are useful as additives in hydrocarbon fuels to prevent and control engine deposits, particularly intake valve deposits. The proper concentration of additive necessary to achieve the desired deposit control varies depending upon the type of fuel employed, the type of engine, and the presence of other fuel additives.

In general, the concentration of the polyalkyl and polyalkenyl aromatic amides of this invention in hydrocarbon fuel will range from about 50 to about 2,500 parts per million (ppm) by weight, preferably from 75 to 1,000 ppm.

When other deposit control additives are present, a lesser amount of the present additive may be used.

The polyalkyl and polyalkenyl aromatic amides of the present invention may be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene, or higher-boiling aromatics or aromatic thinners. Aliphatic alcohols containing about 3 to 8 carbon atoms, such as isopropanol, isobutylcarbinol, n-butanol, and the like, in combination with hydrocarbon solvents are also suitable for use with the present additives. In the concentrate, the amount of the additive will generally range from about 10 to about 70 weight percent, preferably 10 to 50 weight percent, more preferably from 20 to 40 weight percent.

In gasoline fuels, other fuel additives may be employed with the additives of the present invention, including, for example, oxygenates, such as t-butyl methyl ether, anti-knock agents, such as methylcyclopentadienyl manganese tricarbonyl, and other dispersants/detergents, such as hydrocarbyl amines, hydrocarbyl poly(oxyalkylene) amines, or succinimides. Additionally, antioxidants, metal deactivators, and demulsifiers may be present.

In diesel fuels, other well-known additives can be employed, such as pour point depressants, flow improvers, cetane improvers, and the like.

A fuel-soluble, nonvolatile carrier fluid or oil may also be used with the polyalkyl and polyalkenyl aromatic amides of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, and synthetic polyoxyalkylene-derived oils, such as those described, for example, in U.S. Pat. No. 4,191,537 to Lewis and U.S. Pat. No. 4,877,416 to Campbell, and polyesters, such as those described, for example, in U.S. Pat. Nos. 3,756,793 and 5,004,478 to Robinson and Vogel et al., respectively, and in European Patent Application Nos. 356,726 and 382,159, published Mar. 7, 1990 and Aug. 16, 1990, respectively.

These carrier fluids are believed to act as a carrier for the fuel additives of the present invention and to assist in removing and retarding deposits. The carrier fluid may also exhibit synergistic deposit control properties when used in combination with a polyalkyl or polyalkenyl aromatic compound of this invention.

The carrier fluids are typically employed in amounts ranging from about 100 to about 5,000 ppm by weight of the hydrocarbon fuel, preferably from 400 to 3,000 ppm of the fuel. Preferably, the ratio of carrier fluid to deposit control additive will range from about 0.5:1 to about 10:1, more preferably from 1:1 to 4:1, most preferably about 2:1.

When employed in a fuel concentrate, carrier fluids will generally be present in amounts ranging from about 20 to about 60 weight percent, preferably from 30 to 50 weight percent.

EXAMPLES

The following examples are presented to illustrate specific embodiments of the present invention and synthetic preparations thereof; and should not be interpreted as limitations upon the scope of the invention.

EXAMPLE 1

Preparation of 4-Benzyloxybenzoyl chloride

To a flask equipped with a magnetic stirrer and drying tube was added 4-benzyloxybenzoic acid (30.0 grams), anhydrous dichloromethane (200 mL), and then oxalyl chloride (28.7 mL). The resulting mixture was stirred at room temperature for 16 hours and the solvent removed in vacuo to yield 43.2 grams of the desired acid chloride as a white solid.

EXAMPLE 2

Preparation of Bis-N,N'-4-Benzyloxybenzamide of Polyisobutenylethylenediamine

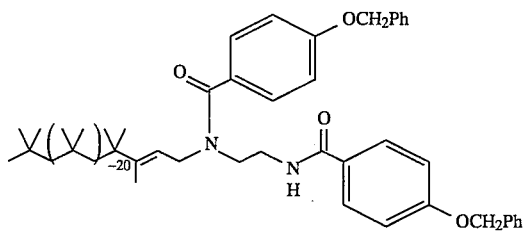

Polyisobutenylethylenediamine having an average of 23 isobutyl units (prepared essentially as described in Example 3 of U.S. Pat. No. 3,960,515) was chromatographed on silica gel eluting with hexane/diethyl ether (1:1) followed by hexane/diethyl ether/methanol/isopropylamine (40:40:15:5). 4-Benzyloxybenzoyl chloride (73.7 grams, prepared as in Example 1) was combined with 193.2 grams of chromatographed polyisobutenylethylenediamine and anhydrous toluene (2 liters). Triethylamine (43.6 mL) and 4-dimethylamino pyridine (8.7 grams) were then added and the resulting mixture was heated to reflux under nitrogen for 16 hours. The reaction was cooled to room temperature and diluted with 3 liters of hexane. The organic layer was washed twice with saturated aqueous sodium bicarbonate solution and once with brine. The organic layer was dried over anhydrous magnesium sulfate, filtered, and the solvents removed in vacuo to yield 264.4 grams of a black oil. The oil was chromatographed on silica gel, eluting with hexane/diethyl ether/isopropylamine (49:49:2) to afford 155.0 grams of the desired product as a brown oil.

EXAMPLE 3

Preparation of Bis-N,N'-4-Hydroxybenzamide of Polyisobutylethylenediamine

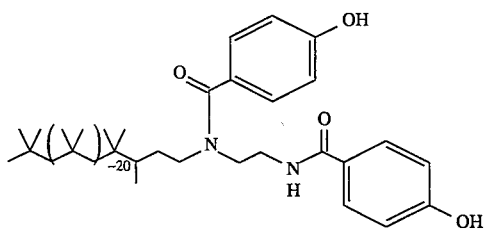

A solution of 155.0 grams of the product from Example 2 in 300 mL of ethyl acetate, 300 mL of acetic acid and 100 mL of toluene containing 15.0 grams of 10% palladium on charcoal was hydrogenolyzed at 35–40 psi for 16 hours on a Parr low-pressure hydrogenator. Catalyst filtration and removal of the residual acetic acid with toluene in vacuo yielded 138.8 grams of the desired product as a brown oil. R (neat) 1609 cm$^{-1}$; $^1$H NMR (CDCl$_3$, D$_2$O) $\delta$7.5–7.7 (m, 4H), 6.5–6.8 (m, 4H), 3.6–4.2 (m, 6H), 0.6–1.6 (m, 183H).

EXAMPLE 4

Preparation of Bis-N,N'-4-Nitrobenzamide of Polyisobutenylethylenediamine

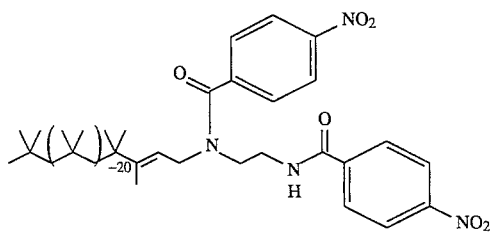

Polyisobutenylethylenediamine having an average of 23 isobutyl units (prepared essentially as described in Example 3 of U.S. Pat. No. 3,960,515) was chromatographed on silica gel eluting with hexane/diethyl ether (1:1) followed by hexane/diethyl ether/methanol/isopropylamine (40:40:15:5). 4-Nitrobenzoyl chloride (5.7 grams) was combined with 20.0 grams of chromatographed polyisobutenylethylenediamine and anhydrous toluene (200 mL). Triethylamine (5.1 mL) was added and the resulting mixture was heated to reflux under nitrogen for 16 hours. The reaction was cooled to room temperature and diluted with 600 mL of hexane. The organic layer was washed twice with saturated aqueous sodium bicarbonate solution and once with brine. The organic layer was dried over anhydrous magnesium sulfate, filtered and the solvents removed in vacuo to yield 23.7 grams of the desired product as a brown oil. $^1$H NMR (CDCl$_3$, D$_2$O) δ8.1–8.35 (m, 8H), 5.4–5.6 (m, 1H), 3.5–4.2 (m, 6H), 0.6–1.8 (m, 180H).

EXAMPLE 5

Preparation of Bis-N,N'-4-Aminobenzamide of Polyisobutylethylenediamine

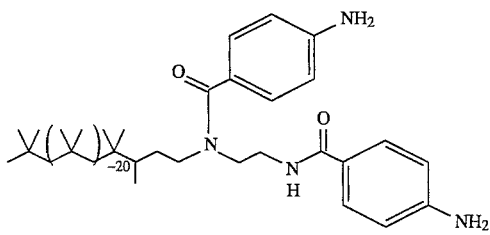

A solution of 18.7 grams of the product from Example 4 in 200 mL of ethyl acetate and 50 mL of toluene containing 4.0 grams of 10% palladium on charcoal was hydrogenated at 35–40 psi for 16 hours on a Parr low-pressure hydrogenator. Catalyst filtration and removal of the residual acetic acid with toluene in vacuo yielded 15.4 grams of the desired product as a brown oil. $^1$H NMR (CDCl$_3$, D$_2$O) δ7.4–7.7 (m, 4H), 6.5–6.8 (m,4H), 3.4–4.0 (m, 6H), 0.6–1.6 (m, 183H).

EXAMPLE 6

Single-Cylinder Engine Test

The test compounds were blended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane, and weighed. The previously determined weight of the clean valve was subtracted from the weight of the value at the end of the run. The difference between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 40° BTC; engine speed is 1,800 rpm; the crankcase oil is a commercial 30W oil.

The amount of carbonaceous deposit in milligrams on the intake valves is reported for each of the test compounds in Table I.

TABLE I

| Sample[1] | Intake Valve Deposit Weight (in milligrams) | | |
| --- | --- | --- | --- |
| | Run 1 | Run 2 | Average |
| Base Fuel | 302.6 | 312.2 | 307.4 |
| Example 3 | 5.7 | 7.2 | 6.5 |
| Example 4 | 112.1 | 127.4 | 118.3 |
| Example 5 | 265.1 | 260.1 | 262.6 |

[1]At 200 parts per million actives (ppma).

The base fuel employed in the above single-cylinder engine tests was a regular octane unleaded gasoline containing no fuel detergent. The test compounds were admixed with the base fuel to give a concentration of 200 ppma (parts per million actives).

The data in Table I illustrates the significant reduction in intake valve deposits provided by the polyalkyl and polyalkenyl aromatic amides of the present invention (Examples 3, 4, and 5) compared to the base fuel.

What is claimed is:

1. A compound of the formula:

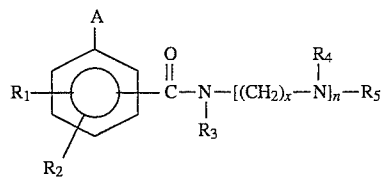

or a fuel-soluble salt thereof;

wherein A is hydroxy, nitro, amino, N-alkylamino wherein the alkyl group contains 1 to 6 carbon atoms, or N,N-dialkylamino wherein each alkyl group independently contains 1 to 6 carbon atoms;

$R_1$ and $R_2$ are each independently hydrogen, hydroxy, lower alkyl having 1 to 6 carbon atoms, or lower alkoxy having 1 to 6 carbon atoms;

$R_3$ is hydrogen or lower alkyl having 1 to 6 carbon atoms;

$R_4$ is hydrogen or an acyl group of the formula:

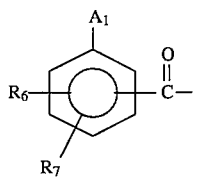

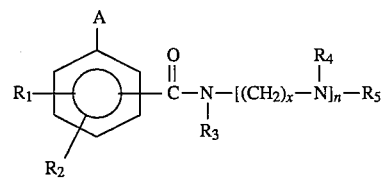

or a fuel-soluble salt thereof;

wherein A is hydroxy, nitro, amino, N-alkylamino wherein the alkyl group contains 1 to 6 carbon atoms, or N,N-dialkylamino wherein each alkyl group independently contains 1 to 6 carbon atoms;

$R_1$ and $R_2$ are each independently hydrogen, hydroxy, lower alkyl having 1 to 6 carbon atoms, or lower alkoxy having 1 to 6 carbon atoms;

$R_3$ is hydrogen or lower alkyl having 1 to 6 carbon atoms;

$R_4$ is hydrogen or an acyl group of the formula:

wherein $A_1$ is hydroxy, nitro, amino, N-alkylamino wherein the alkyl group contains 1 to 6 carbon atoms, or N,N-dialkylamino wherein each alkyl group independently contains 1 to 6 carbon atoms;

$R_6$ and $R_7$ are each independently hydrogen, hydroxy, lower alkyl having 1 to 6 carbon atoms, or lower alkoxy having 1 to 6 carbon atoms;

$R_5$ is a polyalkyl or polyalkenyl group having an average molecular weight in the range of about 450 to 5,000;

n is an integer from 0 to 2; and x is an integer from 2 to 5.

2. The compound according to claim 1, wherein A and $A_1$ are each independently hydroxy, nitro, or amino.

3. The compound according to claim 2, wherein A and $A_1$ are each hydroxy.

4. The compound according to claim 2, wherein A and $A_1$ are each nitro.

5. The compound according to claim 1, wherein $R_1$ and $R_6$ are each independently hydrogen, hydroxy, or lower alkyl having 1 to 6 carbon atoms.

6. The compound according to claim 5, wherein $R_1$ and $R_6$ are each independently hydrogen or hydroxy.

7. The compound according to claim 6, wherein $R_1$ and $R_6$ are hydrogen.

8. The compound according to claim 7, wherein A and $A_1$ are each hydroxy.

9. The compound according to claim 1, wherein $R_l$ and $R_7$ are hydrogen.

10. The compound according to claim 9, wherein $R_3$ is hydrogen.

11. The compound according to claim 1, wherein $R_5$ is a polyalkyl or polyalkenyl group having an average molecular weight in the range of about 500 to 3,000.

12. The compound according to claim 11, wherein $R_5$ is a polyalkyl or polyalkenyl group having an average molecular weight in the range of about 600 to 2,000.

13. The compound according to claim 12, wherein $R_5$ is a polyalkyl or polyalkenyl group derived from polypropylene, polybutene, or polyalphaolefin oligomers of 1-octene or 1-decene.

14. The compound according to claim 13, wherein $R_5$ is derived from polyisobutene.

15. The compound according to claim 1, wherein n is 0 or 1 and x is 2.

16. The compound according to claim 1, wherein n is 1 and x is 2.

17. The compound according to claim 1, wherein n is 0.

18. A fuel composition comprising a major amount of hydrocarbons boiling in the gasoline or diesel range and an effective detergent amount of a compound of the formula:

19. The fuel composition according to claim 18, wherein A and $A_1$ are each independently hydroxy, nitro, or amino.

20. The fuel composition according to claim 18, wherein A and $A_1$ are each hydroxy.

21. The fuel composition according to claim 18, wherein A and $A_1$ are each nitro.

22. The fuel composition according to claim 18, wherein $R_1$ and $R_6$ are each independently hydrogen, hydroxy, or lower alkyl having 1 to 6 carbon atoms.

23. The fuel composition according to claim 22, wherein $R_1$ and $R_6$ are each independently hydrogen or hydroxy.

24. The fuel composition according to claim 23, wherein $R_1$ and $R_6$ are hydrogen.

25. The fuel composition according to claim 24, wherein A and $A_1$ are each hydroxy.

26. The fuel composition according to claim 18, wherein $R_2$ and $R_7$ are hydrogen.

27. The fuel composition according to claim 18, wherein $R_3$ is hydrogen.

28. The fuel composition according to claim 18, wherein $R_5$ is a polyalkyl or polyalkenyl group having an average molecular weight in the range of about 500 to 3,000.

29. The fuel composition according to claim 28, wherein $R_5$ is a polyalkyl or polyalkenyl group having an average molecular weight in the range of about 600 to 2,000.

30. The fuel composition according to claim 29, wherein $R_5$ is a polyalkyl or polyalkenyl group derived from polypropylene, polybutene, or polyalphaolefin oligomers of 1-octene or 1-decene.

31. The fuel composition according to claim 30, wherein $R_5$ is derived from polyisobutene.

32. The fuel composition according to claim 18, wherein n is 0 or 1 and x is 2.

33. The fuel composition according to claim 18, wherein n is 1 and x is 2.

34. The fuel composition according to claim 18, wherein n is 0.

35. The fuel composition according to claim 18, wherein said composition contains about 50 to about 2,500 parts per million by weight of said compound.

36. A fuel concentrate comprising an inert stable oleophilic organic solvent boiling in the range of from about 150° F. to 400° F. and from about to about 70 weight percent of a compound of the formula:

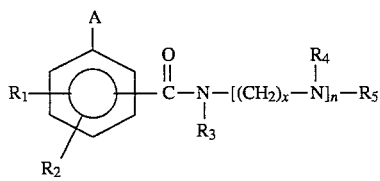

or a fuel-soluble salt thereof;

wherein A is hydroxy, nitro, amino, N-alkylamino wherein the alkyl group contains 1 to 6 carbon atoms, or N,N-dialkylamino wherein each alkyl group independently contains 1 to 6 carbon atoms;

$R_1$ and $R_2$ are each independently hydrogen, hydroxy, lower alkyl having 1 to 6 carbon atoms, or lower alkoxy having 1 to 6 carbon atoms;

$R_3$ is hydrogen or lower alkyl having 1 to 6 carbon atoms;

$R_4$ is hydrogen or an acyl group of the formula:

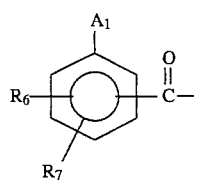

wherein $A_1$ is hydroxy, nitro, amino, N-alkylamino wherein the alkyl group contains 1 to 6 carbon atoms, or N,N-dialkylamino wherein each alkyl group independently contains 1 to 6 carbon atoms;

$R_6$ and $R_7$ are each independently hydrogen, hydroxy, lower alkyl having 1 to 6 carbon atoms, or lower alkoxy having 1 to 6 carbon atoms;

$R_5$ is a polyalkyl or polyalkenyl group having an average molecular weight in the range of about 450 to 5,000;

n is an integer from 0 to 2; and x is an integer from 2 to 5.

37. The fuel concentrate according to claim 36, wherein A and $A_1$ are each independently hydroxy, nitro, or amino.

38. The fuel concentrate according to claim 37, wherein A and $A_1$ are each hydroxy.

39. The fuel concentrate according to claim 38, wherein A and $A_1$ are each nitro.

40. The fuel concentrate according to claim 36, wherein $R_1$ and $R_6$ are each independently hydrogen, hydroxy, or lower alkyl having 1 to 6 carbon atoms.

41. The fuel concentrate according to claim 36, wherein $R_1$ and $R_6$ are each independently hydrogen or hydroxy.

42. The fuel concentrate according to claim 36, wherein $R_1$ and $R_6$ are hydrogen.

43. The fuel concentrate according to claim 42, wherein A and $A_1$ are each hydroxy.

44. The fuel concentrate according to claim 36, wherein $R_2$ and $R_7$ are hydrogen.

45. The fuel concentrate according to claim 36, wherein $R_3$ is hydrogen.

46. The fuel concentrate according to claim 36, wherein $R_5$ is a polyalkyl or polyalkenyl group having an average molecular weight in the range of about 500 to 3,000.

47. The fuel concentrate according to claim 46, wherein $R_5$ is a polyalkyl or polyalkenyl group having an average molecular weight in the range of about 600 to 2,000.

48. The fuel concentrate according to claim 47, wherein $R_5$ is a polyalkyl or polyalkenyl group derived from polypropylene, polybutene, or polyalphaolefin oligomers of 1-octene or 1-decene.

49. The fuel concentrate according to claim 48, wherein $R_5$ is derived from polyisobutene.

50. The fuel concentrate according to claim 36, wherein n is 0 or 1 and x is 2.

51. The fuel concentrate according to claim 36, wherein n is 1 and x is 2.

52. The fuel concentrate according to claim 36, wherein n is 0.

* * * * *